(12) United States Patent
Bartl et al.

(10) Patent No.: US 6,860,990 B2
(45) Date of Patent: Mar. 1, 2005

(54) DEVICE FOR TREATING WATER

(76) Inventors: Ludwig Bartl, Robert-Koch-Strasse 4, 78464 Konstanz (DE); Andrew Cookson, Rheinstrasse 15i, CH-8280 Kreuzlingen (CH); Karel Stefka, Boh. Martinu 28, 602 00 Brno (CZ)

( * ) Notice: Subject to any disclaimer, the term of this patent is extended or adjusted under 35 U.S.C. 154(b) by 67 days.

(21) Appl. No.: 10/182,227

(22) PCT Filed: Jan. 24, 2001

(86) PCT No.: PCT/EP01/00781

§ 371 (c)(1),
(2), (4) Date: Oct. 29, 2002

(87) PCT Pub. No.: WO01/55035

PCT Pub. Date: Aug. 2, 2001

(65) Prior Publication Data

US 2003/0127398 A1 Jul. 10, 2003

(30) Foreign Application Priority Data

Jan. 24, 2000 (DE) .......................................... 100 02 977
Feb. 3, 2000 (DE) .......................................... 100 04 675
Oct. 11, 2000 (DE) .......................................... 100 50 489

(51) Int. Cl.[7] .................................................. C02F 1/46
(52) U.S. Cl. ........................ 210/143; 210/205; 324/439; 204/661; 204/228.6
(58) Field of Search .................................. 210/746, 748, 210/764, 143, 198.1, 205, 243; 422/186.04; 324/439, 450; 204/661, 555, 556, 228.6; 205/743, 751, 753

(56) References Cited

U.S. PATENT DOCUMENTS 3,933,606 A * 1/1976 Harms .......................... 205/743
5,091,152 A * 2/1992 Thomas, Sr. ............. 204/228.6
5,435,894 A * 7/1995 Hayakawa ................... 205/744
6,096,222 A * 8/2000 Wurzburger et al. ........ 210/713
6,179,991 B1 * 1/2001 Norris et al. ................ 205/742
6,245,210 B1 * 6/2001 Nakamura et al. .......... 205/464
6,261,464 B1 * 7/2001 Herrington et al. ......... 210/758
6,270,680 B1 * 8/2001 Silveri et al. ................ 210/746

FOREIGN PATENT DOCUMENTS

DE          3430616 A1  *  2/1986
JP          10-109087 A  *  4/1998

* cited by examiner

*Primary Examiner*—Frank M. Lawrence
(74) *Attorney, Agent, or Firm*—Bachman & Lapointe, P.C.

(57) ABSTRACT

A device for anti-bacterial treatment in particular decontamination and/or sterilisation of water and for killing micro-organisms in water, with a container designed to hold a water quantity intended to be treated and an electrode arrangement which is designed to act on the water quantity in the container and which can be connected and operated with an electrical signal generating device provided outside the container, where the electrical signal generating device can be operated low voltage and is intended to generate an electrical alternating signal between electrodes of the electrode arrangement with a maximum amplitude <50 V and a signal frequency in the range between 1 and 5000 kHz, in particular 5 to 50 kHz, where the signal generating device has an adjustment device designed for automatic changing of a maximum amplitude, an amplitude stroke and/or a signal/pause ratio of the alternating signal as a function of conductance value of the water quantity.

13 Claims, 3 Drawing Sheets

DEVICE FOR TREATING WATER

This application is a 371 of PCT/EP01/00781 filed Jan. 24, 2001.

BACKGROUND OF THE INVENTION

The present invention relates to a device for treatment of water, and in particular a device for the preparation of water by decontamination or sterilisation.

In the context of a simple user-friendly and portable device to improve drinking water quality, so far mainly devices have been available which are based on a filter effect (e.g. by active charcoal filter) or those which by chemical means allow drinking water to be obtained from water-containing fluids contaminated by bacteria, heavy metals etc.

However in practical use purely filter-based solutions for water quantities to be treated which contain bacteria and other micro-organisms have often proved inadequate, and other known processes intended to kill micro-organisms in water e.g. by the application of ultra-violet radiation, have proved unsuitable for use in a portable device not least due to the energy supply required.

Furthermore generic technologies are known from the state of the art which by means of electric signals (typically direct voltages) achieve decontamination or cleaning effects on polluted water. Here the efficacy typically depends on so-called anodic oxidants—typically chlorine—being released from contaminated water by electrolytic effect and in fact it is this chlorine which has the desired bactericidal effect. Usually such known devices therefore have large-surface electrodes in order to achieve the electrolytic effect in the optimum manner.

However such a procedure also has the disadvantage that the released chlorine itself in turn has a negative effect on the water quality in particular in the case of drinking water, and in addition the odour and taste of water treated in this way is typically found to be unpleasant.

The task of the present invention is therefore to create a device for the treatment in particular preparation, decontamination and sterilisation of water which can be operated and applied with low expense, can be constructed to be portable and in addition is universally applicable in relation to its energy supply and allows secure, reproducible and rapidly achievable sterilisation effects but with minimum generation of anodic oxidants.

SUMMARY OF THE INVENTION

The foregoing object is achieved by the device and method of the present invention.

According to the invention advantageously the effect discovered by the inventor is utilised that electrical alternating signals, when introduced to a water quantity to be treated via an electrode, have a decontaminating effect, in particular killing micro-organisms, even if electrolytic effects are largely suppressed and hence the occurrence of anodic oxidants prevented (as can be achieved within the context of the invention by minimised surfaces of the electrodes used).

A critical parameter for maximum efficiency of decontamination by the electrical alternating signal is the fact established by the invention that an optimum amplitude of the alternating signal and optimum signal/pause ratio of the signal (in particular for a rectangular signal), to achieve an optimum effect on the micro-organisms to be eliminated, are dependent on a conductance value of the water.

It is therefore within the framework of the invention to provide a unit for automatic determination of a conductance value of the water quantity to be treated and depending on a result of this conductance value determination then to undertake a corresponding signal adjustment, in particular with regard to frequency, signal amplitude and/or the signal/pause ratio within one period of the alternating signal.

It has also been found by experiment that such an allocation follows a non-linear relationship between the conductance value and maximum signal amplitude, where in particular a parabolic form of a corresponding adjustment curve is preferred.

Advantageously, due to the integration of the water container and the signal generating device for the electrode arrangement in a portable unit, the device can be used as required, flexibly and in particular at locations where there is a requirement for clean decontaminated water.

As in addition for portable flexible use such an easily mobile unit must be largely independent of a power supply network (suitable for large energy quantities), also as part of the present invention the possibility is created to operate the electrical signal generation device with low voltage, where the term "low voltage" in the context of the present invention refers to any voltage less than a mains alternating voltage, which is normally obtained from portable power supply units such as batteries or similar. In particular in the present case the term "low voltage" refers to a voltage of 12, 24 or 30 V but also a voltage of this order of magnitude emitted by common solar cell units.

As a result therefore, with the present invention, for low energy cost a highly efficient decontamination of polluted water and hence conversion into drinking water can be carried out, where the device created according to the invention, due to its portability, can be moved as required and installed at any location.

As part of the invention therefore the term "processing" of the water quantity provided for treatment means not only batch-like operation but also, as will be made clear at a later point in embodiment examples to be described, in particular refers to a design and implementation of the invention as a through-flow device which is covered by the invention where here the container is formed as a through-flow container.

It has been found that application to the water quantity of an alternating signal which has a direct voltage component and which further preferably is a rectified alternating voltage signal (i.e. only has signal components in one polarity) is particularly effective on bacteria. According to a refinement therefore the signal generation device to generate such a signal pattern is designed with direct voltage parts (i.e. a signal pattern which is asymmetrical in relation to the two polarities). Further advantageously an embodiment form of the invention is possible where due to a (periodic) reversal of polarity of the electrode system, undesirable calcification or other undesirable deposits on the electrodes are avoided. According to this preferred refinement of the invention, it is also provided, before each polarity reversal procedure, to insert an asymmetric current-free period of between approximately 1 and 5 seconds in order to prevent further the occurrence of anodic oxidants. Also such pauses have a positive effect on the energy consumption of the arrangement during treatment of contaminated water (utilising the backlash or relaxation effect in water), which is particularly important in portable operation.

In the practical implementation particular importance is devoted to the design of the electrode arrangement where it has proved particularly preferable in a refinement to produce at least one electrode of the electrode arrangement by means of a longitudinally extended conductor (in particular wire), where this wire—with a minimised surface in accordance with the purpose of minimising anodic oxidants—has a typical diameter between approximately 0.1 and 0.5 mm and can suitably be made of platinum or similar materials. Particularly clear with this electrode design is the fundamental difference from known electrolytically-based decontamination processes, where traditionally the electrodes have as large as possible a surface.

For additional treatment of water in relation to heavy metals, nitrates, chlorine compounds etc., the device can also suitably be provided with an additional filter unit where—depending on application and desired intensity of the filter effect—such a filter unit can be connected before a container inlet and/or after a container outlet; it is also possible here to use variable swivellable filters etc.

As part of the present invention the efficacy of the killing of pathogens (protozoa, parasites, bacteria and viruses) in water also depends on a concrete form of the electrical alternating signal introduced by means of the electrode arrangement, where it has proved particularly advantageous to introduce an essentially rectangular alternating signal.

As scientific trials of the present invention have shown, a large number of coliform, mesophilic and psychrophilic bacteria of various types can be killed by the use of the present device in a relatively short treatment time, typically in the range between 5 and 15 minutes, so that the present invention offers a flexible, simple and portable way of cleaning water independently of a mains power supply and hence drastically reduces the risk of infection, in particular in otherwise inadequately supplied areas.

A particularly preferred embodiment of the invention lies in particular in the provision of a multiplicity of containers according to the invention and arranging these in a modular fashion so that several containers lie in parallel to process the water quantity and hence in through-flow operation can increase the cleaning capacity within a predetermined period, and/or can be connected in series in order to create an extended section of effect or application for the water.

Further preferred embodiments of the invention provide that the electrical signal generating device is programmable in relation to the operating times for generation of an electrical alternating signal, where in particular preset programmes with signal and/or operating time patterns can suitable be stored and retrieved.

A further preferred refinement of the invention consists in that at least some electrodes of the electrode arrangement, furthermore preferably those which are provided adjacent to a container outlet, are produced as (furthermore preferably interchangeable) magnesium electrodes in order to allow an additional controlled application of magnesium ions to the water treated according to the invention (approximately 5–15 mg Mg per litre water would be suitable).

For this purpose in general it is suitable to use magnesium electrodes, in particular in relation to a concentration of chloride ions already present in the water quantity: magnesium ions (emerging from the magnesium electrodes) neutralise the chloride to a certain extent, so that in particular in view of the permanently rising chloride concentration in drinking water (and correspondingly rising limit values), an effective treatment of the chloride problem is possible as part of the present invention.

In this context a further advantageous refinement of the invention should be considered in which as a reaction to an increased chloride content previously diagnosed by other known means (e.g. by test strips), manual intervention is possible in the signal generation (as part of the invention, here usually otherwise automatic by the adjustment means): by such intervention in particular a reduction in the maximum amplitude and/or a shortening of the signal duration (in comparison with the pause duration) of the electrical alternating signal could be achieved, with the purpose of reducing the release of chloride caused by the alternating signal.

An alternative possible solution to the chlorine problem as part of the present invention lies in the provision according to a refinement of an additional electrode arrangement with electrodes typically of carbon, magnesium or similar (in particular of metals permissible in drinking water) in the form of rods, a network, coatings or plates, which applies a separate voltage signal, preferably a direct voltage in the range from 1 to 50 V, with an ideal value of 25 V and thus ensures an advantageous neutralisation of chloride-containing water. Such a measure obviates in particular the need for a possible manual intervention according to a refinement as described above in the workings of the adjustment means according to the invention. Suitably the electrodes in the additional electrode arrangement are spaced approximately 1 to 20 mm, ideally 10 mm apart, are present as plates of dimensions of approximately 10×100 mm and are triggered by a current (direct or alternating) in the range between 20 and 100 mA, preferably 20 mA.

BRIEF DESCRIPTION OF THE DRAWINGS

Further advantages, features and details of the invention arise from the description below of preferred examples of embodiments and from the drawings which show.

DETAILED DESCRIPTION

Figure 1:
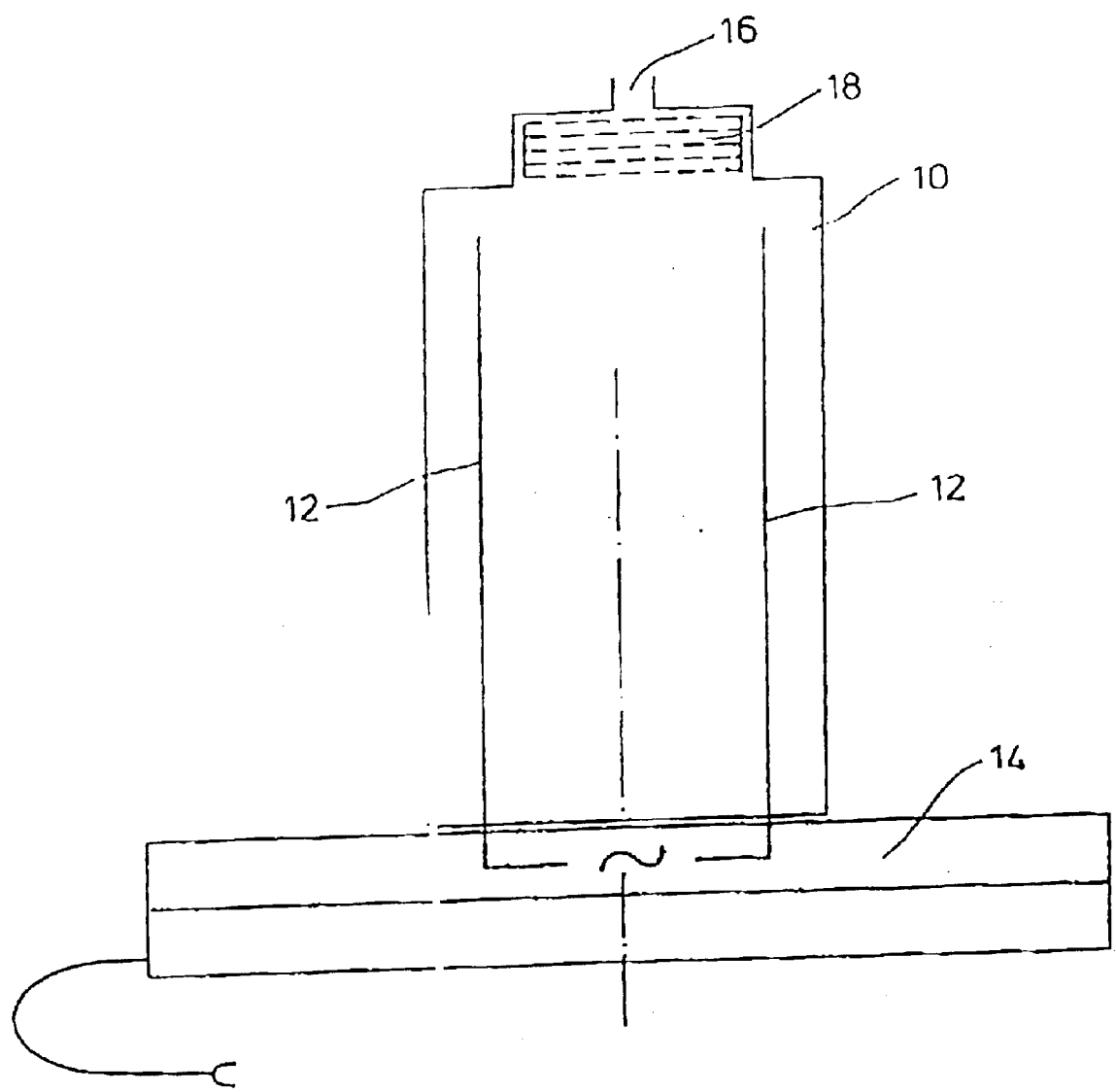
FIG. 1: a diagrammatic side view of the device according to the invention for water treatment.

As shown diagrammatically in FIG. 1, the device according to the invention for the treatment in particular decontamination of water with the purpose of producing drinking water, consists of a cylindrical container unit 10 in the interior of which is provided an electrode arrangement consisting of a pair of wire or rod electrodes 12 of platinum (diameter 0.1 mm) and can thus be contacted, and to the electrodes 12 on the base side can be applied an alternating voltage signal shown diagrammatically.

More precisely, this alternating voltage signal is generated by a signal generating device 14 shown diagrammatically which can itself be connected with a low voltage supply, typically a 12 Volt car battery connection or similar.

At its upper inlet end 16 opposite the signal generator unit 14 is a filter unit 18, also shown diagrammatically, which in an otherwise known manner removes heavy metal ions, chlorine or nitrogen compounds from contaminated water entering through inlet 16 and improves the total cleaning result (alternatively it is quite possible to form the container as a through-flow container by providing a corresponding outlet not shown so that the treatment takes place not in batches but as part of a permanent supply and discharge flow through the inlet and outlet).

In the manner shown in FIG. 1 the decontamination device forms a portable device which can easily also be operated manually, which can be moved to the corresponding locations. Typical capacities of the container unit 10 lie in the range from around 0.5 to 5 litres.

The function of the device shown in FIG. 1 is as follows: the user fills it via the inlet with water to be decontaminated which contains not only heavy metal ions such as lead or copper but also micro-organisms in the form of bacteria, viruses or other potentially harmful pathogens. The water passes through the filter unit 18 and is there filtered in the otherwise known manner and collects in the inside of container unit 10, where particularly preferably the further water treatment is performed only when the container unit 10 is completely filled and hence the rod electrodes 12 lie below the water level in the container 10.

By activating the signal generating unit 14 then an electrical alternating signal is generated and applied to the electrode pair 12, 12, with effect that in the fluid surrounding the electrodes 12 an electrical field is constructed which, taking into account the dielectric contribution of the water, generates a field propagation according to the electrode geometry and the signal form of the alternating signal applied.

Figure 2:
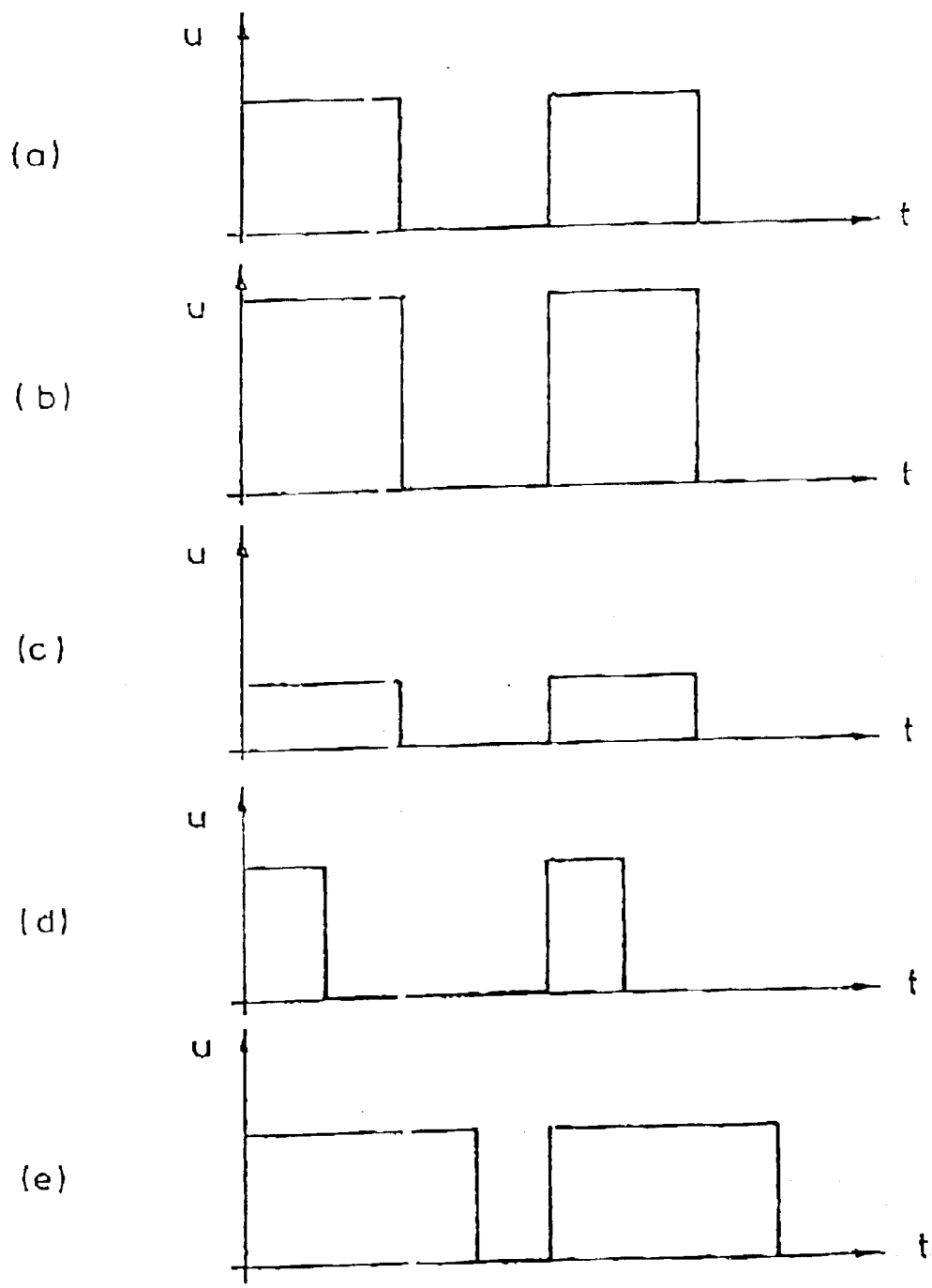
FIG. 2: various signal form diagrams (as functions of the signal voltage over time) of the alternating signal to be introduced via the electrode arrangement into the water quantity to be processed.

FIG. 2 shows various possibilities of applying the alternating signal to the fluid in container 10. The signal forms marked (a) to (e) in FIG. 2 constitute all rectified rectangular alternating signals, thus in the embodiment example shown form only a unipolar signal form (however the present invention is not restricted to either the rectangular signal form shown nor to the unipolarity).

As also the different signal patterns (a) to (e) of FIG. 2 show, as part of the embodiment of FIG. 1 the signal form is preferably made automatically adjustable as a function of a concrete conductance value of the fluid in the container; suitably this conductance value is determined before application of the alternating signal to the fluid or continuously during such application by a measurement process with a unit not shown in the figures.

Depending on the conductance values established, a signal form (signal pattern) optimum for such a fluid is determined, starting as part of a preferred embodiment of the invention from a non-linear although constant (in particular parabolic) relationship between the conductance value and maximum amplitude of the alternating signal.

As shown with examples (a)–(c) in FIG. 2, in concrete terms an automatic conductance—dependent variation of the alternating signal applied can be achieved in that only the maximum amplitude of the alternating signal is changed while the signal/pause ratio of the signal remains unchanged; typically the adjustable maximum amplitude can therefore lie between approximately 3 V (minimum) and 50 V (maximum), where practically—not least limited also by the possibilities of the input signal generated from the low voltage—maximum amplitudes of 12 or 24 V are selected. An example maximum voltage amplitude for low conductivity (in the range from approximately 180 $\mu Scm^{-1}$ and 360 $\mu Scm^{-1}$) is around 30 Volt for voltage pulses of a width of 15 $\mu s$. A higher water conductivity (typically in the range between 1500 $\mu Scm^{-1}$ and 2000 $\mu Scm^{-1}$) would according to this example reduce the voltage amplitude automatically to a value of around 10 Volt with the result of a significant and automatic fall in the average current at higher water conductivity according to the invention.

In addition or alternatively it is possible, see FIGS. 2(d) or (e), instead of the maximum signal amplitude (or in addition there to) to change the signal/pause ratio so that as shown in FIG. 2(e), the signal time within one period no longer corresponds to the pause time (and hence the signal no longer contains the basic oscillation shown in (a) to (c) determined by a signal pulse). Example values for pause times between pulses are around 5 $\mu s$ (for low water conductivity) up to 200 $\mu s$ (for high water conductivity), for typical voltage pulse widths of around 15 $\mu s$.

After measuring the conductivity, according to a preferred embodiment example for relatively highly conductive water (e.g. high concentrations of Ca or Mg ions) the signal amplitude is reduced to a fixed lower limit amplitude (limit voltage), where applicable plus a safety supplement. Such a minimum voltage would—specific to the container or application—be determined by experiment and tested microbiologically, where further parameters for such a limit voltage (limit amplitude) are the concrete container form, the water quantity and electrode parameters such as shape, material and surface area of the electrodes. After setting the maximum amplitude the signal/pause ratio of the alternating signal is set, where in the example described above for relatively highly conductive water, the signal duration is reduced and/or the pause duration extended in the signal-time diagram.

In contrast, measurement of a low conductivity of the water leads to a voltage increase (i.e. increase in maximum amplitude of the alternating signal) and an expansion of the signal duration in relation to the pause duration in the signal-time diagram. In limit cases it is possible that the water to be treated has such a low conductivity that a further electrode must be connected, or ions added to increase the water conductivity, e.g. salts. According to a particularly preferred embodiment these conductivity states or limit states are indicated by a suitable signal e.g. a light signal.

Whereas as shown preferably the signal pattern can be set according to FIG. 2 by automatic control and adjustment of a suitable measurement and adjustment electronics unit, alternatively it is naturally also possible to select manually some preset signal forms using digital technology from a table of preset signal forms, or find other ways of adapting the alternating signal form to a concrete conductance value. In addition or alternatively it is possible within a treatment process to vary the signal frequency, e.g. continuously, between a lower and an upper limit frequency. This take s into account a frequency dependency of the decontamination effect on the various bacteria.

A typical treatment duration of the water quantity processed in FIG. 1 of a volume of 2 litres lies in the range of between 2 minutes and around 20 minutes; depending on degree of contamination however a safety supplement must be added. One particularly preferred refinement of the embodiment in FIG. 1 is also to provide a timer unit (not shown) which ideally with optical or other signal emission informs a user as soon as the preselected decontamination time of the signal application has expired.

In the practical trial of the present invention, the principle according to the invention has proved effective not only also on bacteria of E-coli, salmonella, legionella, enterocos, pseudomonas aerogenosa, staphylococcus aureus etc, and it is also assumed that further protozoa, micro-organisms, parasites, bacteria and viruses in water will be killed or rendered harmless in the described manner.

Also by the device described with filter support, heavy metal ions, lead, cadmium, zinc, copper, arsenic etc. and nitrates, sulphates, hydrocarbons, chlorine, organic chlorine compounds, pesticides etc. can be removed.

According to a further preferred embodiment of the invention it is provided that the container unit according to the invention (e.g. unit 10 in FIG. 1) is itself filled fully or partially with a (non-conductive) filter material so that the container unit, as well as its decontamination effect caused by the electrodes or the electrical signals, also acts as a filter.

According to an example embodiment of this structure of the invention, bulk—where applicable suitably sintered—filter material of a granulation of approximately 0.5 to 1.5 mm is placed in the container according to FIG. 1 and the water treated in described manner. The contaminated water placed in the container was removed after the treatment as fully decontaminated, in addition no living bacteria could be found in the filter material used. This refinement of the invention therefore appears to have considerable potential in particular also for the decontamination of filter units which are known to be breeding grounds for bacteria where no concrete measures against this are taken such as the surface silvering of grains. However in the present invention it should be ensured that the filter material in the container unit does not affect the electrical action due to the own conductivity of the filter material (here for example active charcoal presents potential problems).

In a particularly advantageous manner it is therefore suitable to connect (active charcoal) filter units or similar after the present invention as not only do the excellent treatment or decontamination properties of the present invention ensure that bacterial deposition and hence contamination in the subsequent filter unit can be avoided, but also in practical trials of the present invention a certain sustaining of the treatment effect was observed beyond the container according to the invention, with the result that clearly an indirect treatment action was achieved in the subsequent filter unit with positive effects on the bacteria therein.

Figure 3:
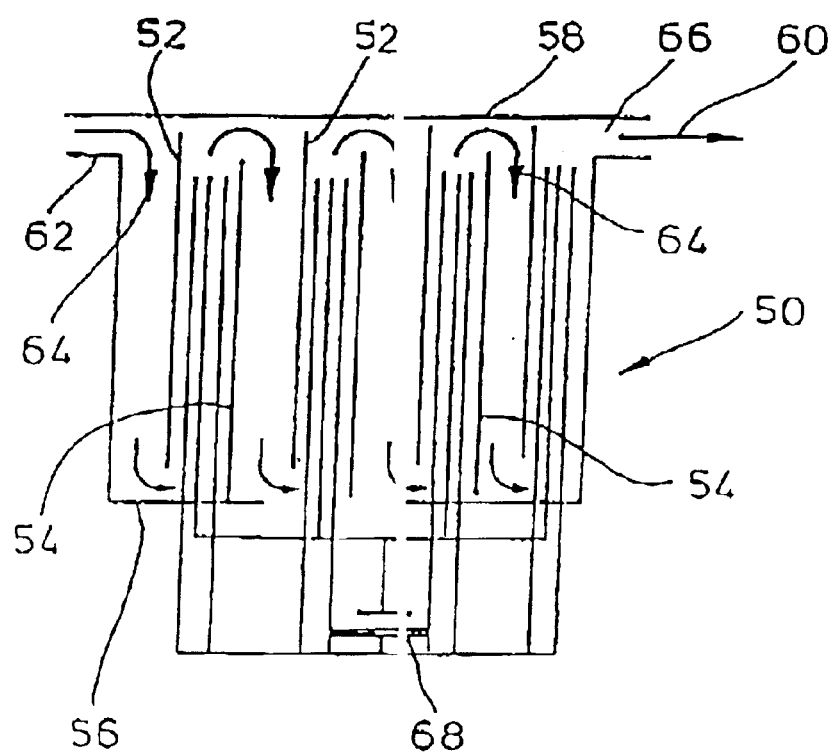
FIG. 3: a further embodiment of the present invention.

With reference to FIG. 3 now a further preferred embodiment of the present invention will be described which is particularly suitable for flexible modular construction and use of the present invention and hence for adaptation to various operating conditions.

FIG. 3 shows a cuboid container body 50 which, as can be seen from the side view of FIG. 3, is formed from a multiplicity of chambers which are separated from each other by intermediate walls 52, 54 extending vertically in the figure from a container base 56 and from a container lid 58 alternately and projecting into the interior of the container 50. More precisely the intermediate walls 52, 54 directed downwards or upwards in the flow direction indicated by arrow 60 in FIG. 3 alternate with each other so that contaminated water entering the container 50 in the left-hand side inlet area 62 is directed alternately upwards and downwards through adjacent chambers in a meander-like direction indicated by the arrow 64 until it reaches a container outlet 66. In addition it can be seen from FIG. 3 that for the purpose of the emergence of the usual gas and air bubbles, the downwards directed intermediates walls 52 do not lie fully on the lid surface 66 of the container 50 but allow a slight gap for gas passage. This venting serves in particular to vent without problems the anodic oxidants present which cannot be prevented in very small quantities.

As can also be seen from FIG. 3 some of the chambers formed in the manner described above have an electrode system designed such that in each case three electrodes formed as platinum wires of a diameter of preferably 0.1 to 0.2 mm project into the intermediate spaces of the container 50 through which water flows upwards according to arrow direction 64. As shown in FIG. 3, the electrode wires are connected with a voltage source 68 shown symbolically and generate signals in the manner described above. In the circuit configuration shown in FIG. 3, the outer electrode wires are connected with a first pole while the inner electrode wire is connected with the other pole of the signal source 68.

The configuration shown in FIG. 3 has proved particularly suitable in particular in regard to positive operating and cleaning properties when namely—surprisingly—the electrodes are placed in the upwards directed water flow.

Whereas in the embodiment example shown, (pure) platinum wires were used as electrodes, other electrode forms are suitable such as for example graphite rods or blocks which, preferably contacted interchangeably, can have typical diameters in the range between 0.1 and 2 mm, preferably around 0.5 mm.

According to a particularly preferred alternative embodiment it is also possible to apply electrodes directly to the walls of the container shown (or another container arrangement), namely by suitable metallisation (or another type of conductor fixing) on the container inner walls so that these not only limit the water container mechanically but also serve as carriers for the electrodes. Such embodiments are preferred in particular in relation to a favourable automatic production of the container arrangements, further preferably in modular construction, where in an otherwise known manner glass plates suitably patterned with the electrode or conductor path structure are configured as walls of the container housing.

In a further refinement of the modular concept it is also suitable to structure the containers similar to the embodiment shown in FIG. 3 (which typically are 3 to 30 cm long and 5 to 15 cm high and have a typical thickness of 20 to 50 mm) so that a multiplicity of these containers can be arranged as modules either in parallel (and hence simultaneously) filled with in-flowing water or as adjacent container modules which can be filled successively with the water to be cleaned. With this technology it is in particular possible to produce a greater number of containers in a standardised size simply and economically and then, by suitable arrangement of a multiplicity to be determined of such modules, combine a number of modules necessary for the suitable cleaning situation and power, without individual container sizes needing to be produced.

According to further preferred embodiments of the invention numerous modifications are possible: the container form is almost unrestricted, as well as the cylindrical form shown it can also have a cuboid, ellipsoid form etc. The electrodes, as well as the positions shown inside the container, can also be direct parts of the container wall e.g. as a network (e.g. made of carbon fibres) applied directly to the container inner wall, alternatively as platinum foil.

A further alternative embodiment of the invention is achieved by separating the electrodes from the medium e.g. by corresponding membrane material (ion-permeable material).

By experiment it was found that the decontamination effect according to the invention can be increased by the effect of pressure or blowing for a predetermined period.

Great differences in the conductivity of the water can be made more treatable also by the application of additional ions by cooking salt, calcium or magnesium salts; high water conductivity may require special electrode forms.

If the water to be cleaned in extreme cases is heavily biologically contaminated, as part of the invention it is possible to connect before or after this further purification, flocculation and/or ventilation stages and filtration steps.

Although a key application of the present invention lies in the portable sector and accordingly suitable low voltages are used, the present invention is not however restricted to a simply portable operation and in particular with the use of suitable voltage converters or power packs it is possible to operate the present invention stationary. In particular in such a case when namely mains voltage is available, according to a further preferred embodiment it is provided to use the existing mains voltage to operate a cooling device for the container according to the invention with further advantageous effects on the hygiene conditions in the container.

Finally it should be emphasised that with the present invention, as intended, the occurrence of anodic oxidants in particular chlorine can be largely avoided. Not least this effect is also the result of the automatic adjustment and changing of the alternating signals according to the invention as a function of the actual water conductivity, which advantageously in particular also leads, on implementation of the invention as a through-flow system, to water being drinkable immediately after treatment without the absorption of free chlorine in active charcoal filters or similar. Experimental tests on the chlorine content or occurrence of chlorine by the treatment according to the invention have shown that for bacterially contaminated water with typically low quantities of 1 mg chloride per litre water, no free chlorine was measured; for typical (normal) contents of around 10 mg chloride per litre water, after treatment no free chlorine was found; and finally for bacterially contaminated water with a high chloride content (with 120 mg chloride per litre water which is above the normal limit of 100 mg/litre) after treatment according to the invention a free chlorine content in the outlet <0.1 mg per litre was found, which lies far below the permitted chlorine content for drinking water.

What is claimed is:

1. A device for anti-bacterial treatment, in particular decontamination and/or sterilisation of water and for killing micro-organisms in water, comprising a container formed to hold a water quantity intended to be treated, an electrode arrangement which acts on the water quantity in the container and is connected and operated with an electrical signal generating device provided outside the container, wherein the electrical signal generating device is operated with low voltage and is designed to generate an electrical alternating signal between electrodes of the electrode arrangement with a maximum amplitude <50 V and a signal frequency in the range between 1 and 5000 kHz, the signal generating device includes adjustment means which are designed for automatically changing a maximum amplitude, an amplitude stroke and/or a signal to pause ratio of the alternating signal as a function of a conductance value of the water quantity, wherein the container and the signal generating device form a portable unit and the electrode arrangement comprises at least one of (1) an at least partly longitudinally elongated wire shaped conductor as an electrode and (2) an electrode configured as a wire shaped pattern on a wall of the container.

2. A device according to claim 1, wherein the electrical alternating signal has a direct voltage component and is a rectified alternating voltage signal.

3. A device according to claim 1, wherein the electrode arrangement comprises an electrode having a maximum diameter of 0.5 mm.

4. A device according to claim 1, wherein the electrode arrangement is made of a magnesium material so that, for a given chloride content in the water quantity to be treated, magnesium ions can enter the water quantity during treatment.

5. A device according to claim 1, wherein the adjustment means are formed so that for a low conductance value of the water quantity a voltage amplitude of the alternating signal is increased and for a high conductance value the voltage is reduced.

6. A device according to claim 1, wherein the adjustment means are formed so that for a low conductance value of the water quantity a time period between successive pulses of the alternating signal is set to a low value and for a high conductance value the time interval is set to a higher value.

7. A device according to claim 1, wherein a filter unit is connected at least one of upstream of a container inlet of the container and downstream of a container outlet of the container.

8. A device according to claim 1, wherein the container is at least partly filled with a filter material and itself acts as a filter, where the electrode arrangement provided in the container serves for decontamination or sterilisation of the container serving as a filter.

9. A device according to claim 1, wherein the adjustment means of the signalling device includes means for manual intervention for manually changing the maximum amplitude, amplitude stroke and/or signal/pause ratio of the alternating signal as a function of a previously measured chloride content in the water quantity.

10. A device according to claim 1, further including means for electronic determination of an electrical conductance value of the water quantity, wherein the means are connected with the signal generating device so that as a reaction to a predetermined conductance value, the signal generating device sets and emits an associated signal pattern of the electrical alternating signal, and where the signal pattern is allocated to the conductance value along a non-linear adjustment or calibration curve and/or according to predetermined discrete and stored parameters.

11. A device according to claim 1, further including an additional electrode arrangement to which can be applied a separately applicable direct or alternating voltage and which contains carbon, magnesium and/or a noble metal and is arranged such that its effects can neutralise or eliminate anodic oxidants, in the water.

12. A device according to claim 1, wherein a multiplicity of cuboid containers are provided modular and can be configured so that the water quantity provided for treatment can flow through a multiplicity of the modular containers simultaneously or can flow through the multiplicity of modular containers sequentially.

13. A device according to claim 1, wherein the electrical signal generating device is connected with a programmable time control unit which predetermines setting of operating times of the electrical signal generating device.

\* \* \* \* \*